United States Patent [19]

Aldridge et al.

[11] 4,145,437
[45] Mar. 20, 1979

[54] HYDROXY ACIDS

[75] Inventors: David C. Aldridge; Graham C. Crawley; Colin J. Strawson, all of Macclesfield, England

[73] Assignee: Imperial Chemical Industries Limited, London, England

[21] Appl. No.: 845,420

[22] Filed: Oct. 25, 1977

Related U.S. Application Data

[63] Continuation of Ser. No. 716,284, Aug. 20, 1976, Pat. No. 4,070,480.

[30] Foreign Application Priority Data

Aug. 21, 1975 [GB] United Kingdom ............... 34842/75

[51] Int. Cl.$^2$ ................. C07D 307/32; A61K 31/365
[52] U.S. Cl. .................................. 424/279; 260/343.6
[58] Field of Search ...................... 260/343.6; 424/279

[56] References Cited
PUBLICATIONS

Beereboom, et al., Jour. Org. Chem. 1965, 30, 1231–1233.
H. Stobbe, Annalen. 1899, 308, 144–155, R Fittig Annalen, 1899, 305, 1–18, R. Fittig Annalen, 1899, 304, 311–325.
McCorkindale et al., Tetrahedron letters, No. 6, pp. 727–730.
Mukaiyama et al., Bull. Chem. Soc. of Japan, vol. 44, No. 1, 1971.

Primary Examiner—Natalie Trousof
Assistant Examiner—Jane T. Fan
Attorney, Agent, or Firm—Cushman, Darby & Cushman

[57] ABSTRACT

The invention concerns novel racemic and optically active mono- and di-hydroxy alkanoic acids bearing phenyl and/or alkyl substituents, processes for their preparation, and pharmaceutical compositions for therapeutic use in the treatment of duodenal or gastric ulcers. Representative compounds of the invention are 2-(5β-n-butyl-4β-hydroxy-2-oxo-tetrahydrofuran-3β-yl)-2α-methyl-acetic acid and 3α-methyl-5β-(1β-hydroxy-n-pentyl)-2-oxo-tetrahydrofuran-4β-ylcarboxylic acid.

6 Claims, No Drawings

HYDROXY ACIDS

This is a continuation of application Ser. No. 716,284, filed Aug. 20, 1976, now U.S. Pat. No. 4,070,480.

This invention relates to acids and in particular it relates to hydroxy acids which possess ulcer-healing properties.

According to the invention there is provided a hydroxy acid of the formula:

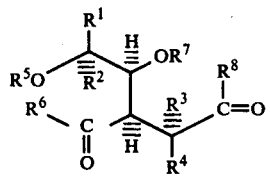

wherein one of $R^1$ and $R^2$ is hydrogen, a $C_{1-10}$-alkyl or phenyl radical, and the other of $R^1$ and $R^2$ is hydrogen; one of $R^3$ and $R^4$ is hydrogen or a $C_{1-6}$-alkyl radical and the other of $R^3$ and $R^4$ is hydrogen; or $R^3$ and $R^4$ together form the methylene ($=CH_2$) radical; and wherein either $R^5$ is hydrogen and $R^6$ is a hydroxy radical or $R^5$ and $R^6$ together form a direct bond; and either $R^7$ is hydrogen and $R^8$ is a hydroxy radical or $R^7$ and $R^8$ together form a direct bond; provided that at least one of $R^5$ and $R^7$ is hydrogen; or a pharmaceutically-acceptable salt thereof.

It will be observed that the hydroxy acids of formula I contain at least two asymmetric carbon atoms, namely the carbon atom bearing the radical —$OR^7$ and that bearing the radical —$CO.R^6$. In addition the hydroxy acids may contain up to two more asymmetric carbon atoms depending on the nature of the radicals $R^1$, $R^2$, $R^3$ and $R^4$. As a consequence a hydroxy acid of formula I can be isolated in racemic forms and optically active forms. This specification is addressed to any racemic or optically active form of a hydroxy acid of formula I which shows the above useful properties; it being a matter of common general knowledge how to obtain an optically active form by resolution or synthesis from optically active starting materials and how to determine the biological properties of the optical isomers, for example, by the test referred to later.

It is to be understood that this specification is only addressed to those hydroxy acids of formula I which have the indicated relative stereochemistry at the carbon atoms bearing the radical —$OR^7$ and —$CO.R^6$ respectively. It is also to be understood that the absolute configuration of a hydroxy acid of formula I may in fact be the mirror image of that shown in formula I.

A particularly suitable value for $R^1$ or $R^2$ when it is a $C_{1-10}$-alkyl radicals is, for example, a methyl, ethyl, propyl, butyl, pentyl, hexyl, octyl or decyl radical. A straight chain $C_{1-10}$-alkyl radical is preferred, for example, a methyl, ethyl, n-propyl, n-butyl, n-pentyl, n-hexyl, n-octyl or n-decyl radical.

A particularly suitable value for $R^3$ or $R^4$ when it is a $C_{1-6}$-alkyl radical is, for example, a methyl, ethyl, propyl or butyl radical. A straight chain $C_{1-6}$-alkyl radical is preferred, for example, a methyl, ethyl, n-propyl or n-butyl radical.

A particular group of compounds of the invention comprises those hydroxy acids of formula I wherein $R^5$ and $R^6$ together form a direct bond, that is mono-lactones of the formula:

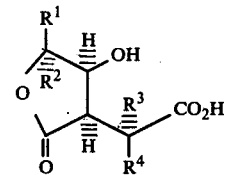

wherein $R^1$, $R^2$, $R^3$ and $R^4$ have the meanings stated above; and the pharmaceutically-acceptable, base addition salts thereof.

A second particular group of compounds of the invention comprises those hydroxy acids of formula I wherein $R^7$ and $R^8$ together form a direct bond, that is mono-lactones of the formula:

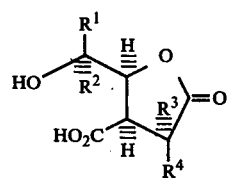

wherein $R^1$, $R^2$, $R^3$ and $R^4$ have the meanings stated above; and the pharmaceutically-acceptable, base addition salts thereof.

A third particular group of compounds of the invention comprises those hydroxy acids of formula I wherein $R^5$ and $R^7$ are both hydrogen, that is diacids of the formula:

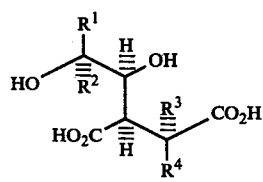

wherein $R^1$, $R^2$, $R^3$ and $R^4$ have the meanings stated above; and the pharmaceutically-acceptable base addition salts thereof.

A further particular group of compounds of the invention comprises those hydroxy acids of formula I wherein $R^1$ is a phenyl or an n-butyl radical, $R^2$ is hydrogen, one of $R^3$ and $R^4$ is a methyl radical, and the other of $R^3$ and $R^4$ is hydrogen, and the pharmaceutically-acceptable base salts thereof. Within this particular group, a further preferred group of compounds of the invention comprises those compounds of formula II or III wherein $R^1$, $R^2$, $R^3$ and $R^4$ have the meanings stated immediately above.

A particularly suitable pharmaceutically-acceptable base addition salt is, for example, an ammonium salt, an alkali metal or alkaline earth metal salt, for example a sodium, potassium, magnesium or calcium salt, or an aluminium salt, or a salt with an organic base, for example an aliphatic or cycloaliphatic amine, for example meglumine (1-methylamino-1-deoxy-D-glucitol), diethylamine, triethylamine or morpholine. When in the compound of formula I, both $R^6$ and $R^8$ are hydroxy radicals, the base addition salt may be formed with only one equivalent of base to neutralise only one of the two carboxy groups in the compound of formula I.

For convenience of notation throughout this specification, the hydrogen atoms attached to the carbon atoms bearing the radical —OR$^7$ and —CO.R$^6$ respectively in formula I, together with the radicals R$^2$ and R$^3$ in all the formula drawings, will be designated as in the α-configuration. The radicals R$^1$ and R$^4$ will consequently be designated as in the β-configuration.

Particular compounds of the invention are described in the Examples; and of these the following are particularly preferred:

2-(5β-n-butyl-4β-hydroxy-2-oxo-tetrahydrofuran-3β-yl)-2α-methyl-acetic acid and 2-(5β-phenyl-4β-hydroxy-2-oxo-tetrahydrofuran-3β-yl)-2β-methyl-acetic acid, (that is the compounds of formula II wherein R$^1$ is n-butyl, R$^2$ and R$^4$ are hydrogen and R$^3$ is methyl; and wherein R$^1$ is phenyl, R$^2$ and R$^3$ are hydrogen, and R$^4$ is methyl, respectively); and 3α-methyl-5β-(1β-hydroxy-n-pentyl)-2-oxo-tetrahydrofuran-4β-ylcarboxylic acid and 3β-methyl-5β-(β-phenyl)hydroxymethyl-2-oxo-tetrahydrofuran-4β-ylcarboxylic acid, (that is the compounds of formula III wherein R$^1$ is n-butyl, R$^2$ and R$^4$ are hydrogen, and R$^3$ is methyl; and wherein R$^1$ is phenyl, R$^2$ and R$^3$ are hydrogen, and R$^4$ is methyl, respectively); or a pharmaceutically-acceptable base addition salt thereof.

The hydroxy acids of the invention may be manufactured by methods known in themselves for the manufacture of chemically analogous compounds. Such processes are exemplified by the following in which R$^1$, R$^2$, R$^3$, R$^4$, R$^5$, R$^6$, R$^7$ and R$^8$ have the meanings defined above, unless otherwise specified:

(a) Hydrolysing a dilactone of the formula:

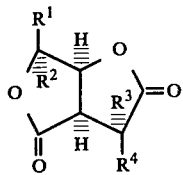

V under basic conditions. The precise product obtained from the hydrolysis, that is the mono-lactone of formula II or III or the di-acid of formula IV as defined above, depends upon the basic conditions used. In general, for a particular dilactone starting material, a mono-lactone of formula II or III as defined above is obtained under milder basic conditions than those required to give the corresponding di-acid of formula IV. Thus, for example, when a dilactone of formula V wherein R$^1$ is n-butyl, R$^2$ and R$^4$ are hydrogen, and R$^3$ is methyl, that is the known compound dihydrocanadensolide, is hydrolysed with an excess of 3N sodium hydroxide solution at 20°–25° C. for 3 hours the corresponding di-acid of formula IV is obtained, whereas hydrolysis at pH 9–10 for 1 hour gives the corresponding mono-lactones of the formula II and III respectively.

The reaction may be carried out at, for example, 0°–60° C., but in general is preferably carried out at, for example 0°–30° C.

The reaction is conveniently carried out in a polar organic solvent, for example aqueous ethanol, methanol, acetonitrile or acetone.

The basic conditions are conveniently supplied by, for example, an inorganic base, for example an alkali metal hydroxide, for example sodium or potassium hydroxide. A pH of 9–10 is preferred when a monolactone of formula II or III is required.

The above mentioned dilactone starting material, dihydrocanadensolide, is a known compound and may be obtained by fermentation of the organism *Penicillium canadense* (McCorkindale et alia, Tetrahedron Letters, 1968, 727). A related known dilactone starting material, canadensolide, that is a compound of formula V wherein R$^1$ is n-butyl, R$^2$ is hydrogen, and R$^3$ and R$^4$ together form the methylene radical, is also described by McCorkindale et alia.

The remaining dilactone starting materials of formula V are also known and are described, together with procedures for their preparation, in Offenlegungsschrift No. 2543150.

(b) Removing a carboxylic acid protecting group from a compound of the formula:

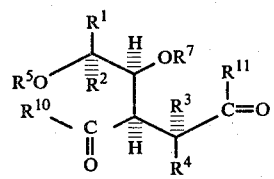

VI wherein R$^{10}$ is a carboxylic acid protecting group and R$^5$ is hydrogen, or R$^5$ and R$^{10}$ together form a direct bond; and R$^{11}$ is a carboxylic acid protecting group and R$^7$ is hydrogen, or R$^7$ and R$^{11}$ together form a direct bond; provided that at least one of R$^5$ and R$^7$ is hydrogen.

A particularly suitable value for R$^{10}$ or R$^{11}$ when it is a carboxylic acid protecting group is, for example, a C$_{1-4}$-alkoxy radical for example a methoxy, ethoxy or butoxy radical; a phenoxy or benzyloxy radical optionally bearing 1–3 substituents selected from halogen atoms, for example chlorine or bromine atoms, methyl, methoxy and nitro radicals; or a phenacyloxy radical.

The particular reaction conditions for the removal of a specific carboxylic acid protecting group necessarily depend on the precise chemical structure of the group. Thus, whereas C$_{1-4}$alkoxy, phenoxy and substituted phenoxy and phenacyloxy radicals are preferably removed under basic conditions, by contrast benzyloxy and substituted benzyloxy radicals are preferably removed under reductive conditions.

Particularly suitable basic conditions are provided by, for example, aqueous sodium or potassium hydroxide at pH 9–10 at 0°–50° C., optionally together with a polar organic solvent, for example methanol, ethanol or acetonitrile. When a mono-lactone of formula II or III is required the basic conditions employed must necessarily be as mild as possible to limit the hydrolysis of the lactone ring, and an especially labile carboxylic acid protecting group is preferred, for example, a phenoxy or a substituted phenoxy radical, or a phenacyloxy radical.

Particularly suitable reductive conditions are provided by, for example, hydrogenation at or near atmospheric pressure, in the presence of a palladium or platinum catalyst at 0°–30° C., optionally in an organic solvent, for example ethanol.

The starting materials of formula VI may be made by methods known in themselves for the synthesis of chemically analogous compounds. Thus, for example, when both R$^5$ and R$^7$ are hydrogen, they may be made by oxidative hydroxylation of the double bond of a compound of the formula:

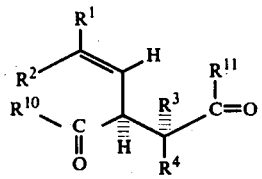

wherein $R^{10}$ and $R^{11}$ have the meanings stated above, using the procedure generally described in Offenlegungsschrift No. 2543150.

In a similar manner, for example, oxidative hydroxylation of the double bond in a compound of the formula:

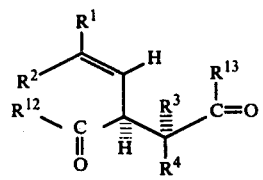

wherein one of $R^{12}$ and $R^{13}$ is a hydroxy radical and the other of $R^{12}$ and $R^{13}$ is a carboxyl protecting group as defined above, followed by acid catalysed cyclisation of the dihydroxy product, may be used to obtain the remaining starting materials of formula VI.

A particularly convenient starting material of formula VI wherein $R^7$ is hydrogen, and $R^5$ and $R^{10}$ together form a direct bond and $R^{11}$ is a carboxylic acid protecting group as defined above other than a benzyloxy or substituted benzyloxy radical, is obtained by reduction of the corresponding tetronic acid of the formula:

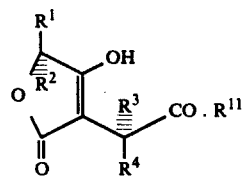

wherein $R^{11}$ has the meaning stated immediately above.

Alternatively since the starting materials of formula VI are esters, they may be obtained, for example, by conventional esterification of an hydroxy acid of formula I obtained by any of processes (a), (c), (d) or (e) herein. The esterification is preferably carried out under mild conditions such that simultaneous lactonisation is prevented. Thus, for example the sodium salt of an acid of formula I may be reacted with the corresponding chloro-, bromo-, or iodo- derivative of the carboxylic acid protecting group, for example, with iodomethane, benzyl bromide or a substituted benzyl bromide.

(c) For the manufacture of a hydroxy acid of formula I wherein both of $R^5$ and $R^7$ are hydrogen, that is, a di-acid of formula IV, hydrolysing a hydroxy acid of formula I wherein only one of $R^5$ and $R^7$ is hydrogen, that is, a mono-lactone of formula II or III, under basic conditions.

This process is carried out under essentially similar basic conditions and optionally in the presence of the same solvents and at the same temperature as the process (a) described herein above. It will be recognised that the necessary starting materials of formula II or III are products of the processes (a), (b), (d) and (e) described herein.

(d) For the manufacture of a hydroxy acid of formula I wherein only one of $R^5$ and $R^7$ is hydrogen, that is, a mono-lactone of formula II or III, cyclising a hydroxy acid of formula I wherein both of $R^5$ and $R^7$ are hydrogen, that is a di-acid of formula IV, under acidic conditions.

The reaction is preferably carried out in a suitable organic solvent, for example acetone, and conveniently at a temperature of, for example, 20°–80° C.; for example at reflux temperature. The acidic conditions may be provided by the addition of a catalytic amount of acid, for example a mineral acid, for example hydrochloric acid. Alternatively, and this is preferred, the acid conditions may be provided by the inherent acidity of the hydroxy acid starting material.

It will be recognised that cyclisation of the starting di-acid can also give rise to the corresponding dilactone. The reaction should therefore be stopped when the yield of the desired compound of formula II or III is acceptable.

(e) For the manufacture of a hydroxy acid of formula I wherein $R^5$ and $R^6$ together form a direct bond, that is, a monolactone of formula II, reducing a tetronic acid of the formula:

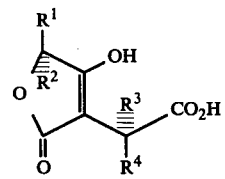

The reduction is conveniently carried out, for example, with hydrogen at or near atmospheric pressure in the presence of a suitable catalyst, for example rhodium on an alumina support at 0° to 30° C., optionally in an organic solvent, for example ethanol.

The starting material of formula X may be obtained by hydrolysis of the corresponding methyl or ethyl ester, itself obtained by standard synthetic procedures known in the art.

Whereafter, when a pharmaceutically-acceptable base addition salt as defined above is required, an hydroxy acid of formula I is reacted with a suitable base, using conventional procedures.

As stated above, the compounds of formula I possess ulcer healing properties. These properties may be demonstrated by the oral or sub-cutaneous administration of a test compound to rats in which duodenal ulceration has been produced by application of acetic acid to the duodenum. Activity is assessed on the basis of a substantial reduction in the size, or incidence of duodenal ulcers as compared with the ulcers of an undosed control group. In this test the compounds of formula I show activity at a daily dose of 25 mg./kg. or less. The test is carried out over a period of 21 days and in this time no signs of overt toxicity were observed with any of the compounds of formula I at the active dose.

When used to produce an ulcer healing effect in warm blooded animals, a compound of formula I is administered at a daily oral or subcutaneous dose of 50 mg./kg. or less, preferably from 0.25 to 5 mg./kg., repeated if necessary at 4–5 hourly intervals. In man this is equivalent to a dose of 12.5–250 mg., four times per day.

The compounds of formula I are used in the form of pharmaceutical compositions comprising a compound of formula I and a pharmaceutically-acceptable diluent or carrier. Such pharmaceutical compositions are provided as a further feature of the invention.

A particularly suitable composition may be in a form suitable for oral administration, for example in the form of a tablet, capsule, aqueous suspension, oily solution or suspension, emulsion, dispersible powder, granule, syrup or elixir; or for parenteral administration, for example in the form of a sterile injectable aqueous solution or suspension, or oily solution or suspension; or for rectal administration, as a suppository. The compositions may be obtained using conventional excipients and by generally conventional means, except that it is preferable that heating at a temperature much greater than 25° C. should be avoided. A convenient unit dose for oral or subcutaneous administration contains from 5-200 mg. of a compound of formula I or an equivalent amount of a pharmaceutically-acceptable base addition salt thereof.

Tablets may either be uncoated or they may be coated by known means with a film of a agent which is known to increase their stability or to modify their disintegration and absorption in the gastro-intestinal tract. Such agents are for example, hydroxypropylmethyl cellulose and hydroxypropylmethylcellulose phthalate.

When the composition is in an aqueous form, it is desirable that the pH of the aqueous composition should be in the range 6-8 and preferably 7.0-7.5.

In addition to a compound of formula I, the pharmaceutical compositions may contain one or more agents known to be of value in the treatment of ulcers and compatible with the compound of formula I. Thus, for example the pharmaceutical compositions may contain one or more of the following agents in addition to a compound of formula I: an antacid for example magnesium trisilicate, and anti-foaming agent for example simethicone, an inhibitor of gastric secretion for example cimetidine, or a prostaglandin derivative, especially of the E-series.

A compound of formula I may also be advantageously combined in a pharmaceutical composition together with an anti-inflammatory agent, for example, aspirin, indomethacin or naproxen, since it is well known that anti-inflammatory agents produce irritation and ulceration in the gastro-intestinal tract, as a side-effect.

The invention is illustrated, but not limited, by the following Examples, in which:

(i) — All evaporations unless stated otherwise were carried out by rotary evaporation under reduced pressure at ≦20° C.;

(ii) — Petroleum ether (b.p. 60°-80° C.) is referred to as "petrol";

(iii) — NMR spectral data was determined at 100 MH$_z$ using tetramethylsilane as an internal reference and the conventional abbreviations for complex interactions are used, for example: m: multiplet, d: doublet, t: triplet, q: quartet.

(iv) — TCAI stands for trichloroacetyl isocyanate.

EXAMPLE 1

Optically active dihydrocanadensolide, 6β-butyl-3α-methyl-3α,3aα,6α,6aα-tetrahydrofuro[3,4-b]furan-2,4-dione, (5.0g.) was dissolved in methanol (100ml.) at 20°-25° C. and water (25ml.) was added. The pH of the solution was adjusted to 9 and maintained at that pH for 1 hour by dropwise addition of 0.2 N aqueous sodium hydroxide. The pH was then adjusted to 7 with aqueous N-hydrochloric acid, and the solution evaporated to dryness at 20°-25° C. under reduced pressure. The residue was dissolved in 0.1 M aqueous citric acid/0.2 M aqueous disodium hydrogen phosphate buffer (500ml.) at pH 4, and the solution was extracted three times with ethyl acetate (250ml. each time). The combined extracts were dried over sodium sulphate and evaporated to dryness at 20°-25° C. under reduced pressure. The residue was dissolved in acetone (10ml.) and petrol was added dropwise to the stirred solution to give a crystalline precipitate of 3α-methyl-5β-(1β-hydroxy-n-pentyl)-2-oxo-tetrahydrofuran-4β-ylcarboxylic acid, $[\alpha]_D^{28}$ −116° (c, 2.7, MeOH), m.p. 112°-114° C. This compound was further purified by the laboratory temperature precipitation from acetone/petrol described above to give material of $R_f$ 0.44 (on silica gel 0.2 mm. plates, developed in chloroform:methanol: acetic acid, 90:5:5).

EXAMPLE 2

Optically active dihydrocanadensolide (2.0g.) was suspended in 3N aqueous sodium hydroxide (20ml.) and stirred at 20°-25° C. for 3 hours. The pH of the resulting solution was adjusted to 3.5 with concentrated aqueous hydrochloric acid, and 0.1 M aqueous citric acid (20ml.) was added. The solution was extracted three times with ethyl acetate (50ml. each time), and the combined extracts dried over sodium sulphate and evaporated to dryness at 20°-25° C. under reduced pressure. The residue was dissolved in acetone (50ml.) and petrol was added with stirring to give a pure crystalline precipitate of 2α-methyl-3β-carboxy-4β,5β-dihydroxynonanoic acid $[\alpha]_D^{28}$ + 18 (c, 3.07, MeOH), m.p 132°-133° C. Thin layer chromatography $R_f$− 0.13 (using silica gel 0.2mm. plates, eluant as in Example 1).

EXAMPLE 3

(±)-6β-n-Butyl-3,3aβ,6aα-tetrahydrofuro[3,4-b]furan-2,4-dione (413mg.) was dissolved in a solution (200ml.) containing 8% v/v acetonitrile in water. The solution thus obtained was adjusted to pH 10 at 25° C. by addition of aqueous 0.1N sodium hydroxide solution. The solution was controlled at pH 10 and 25° C. for 10 minutes by further addition of aqueous 0.1N sodium hydroxide using a pH-meter to monitor the pH of the solution.

The solution was then acidified to pH 6 with aqueous 0.1N hydrochloric acid and evaporated to dryness. The residue was dissolved in a pH 4.0 buffer solution (30ml.) [prepared from aqueous 0.1M citric acid solution (12.29 parts by volume) and aqueous 0.2M disodium phosphate solution (7.71 parts by volume)], and the solution was extracted with ethyl acetate (3 × 20ml.). The combined extracts were dried (Na$_2$SO$_4$) and evaporated. The resultant oil solidified after trituration with chloroform to give a white solid which was recrystallised from a cold mixture of ethyl acetate and petrol. There was thus obtained (±)-(5β-n-butyl-4β-hydroxy-2-oxo-tetrahydrofuran-3-β-yl)acetic acid, m.p. 138°-140° C., having the following characteristic NMR spectrum:

| | $d_6$-acetone | | | | $d_6$-acetone + TCAI | | |
|---|---|---|---|---|---|---|---|
| Signal | δ | Type | Proton No. | Coupling Constant ($H_z$) | δ | Type | Coupling Constant ($H_z$) |
| 5β-n-Butyl | 0.9–1.8 | m | 9 | | 0.9–1.8 | m | |
| 5α-H | 4.50 | m | 1 | | 4.75 | dt | $J_1 = 3, J_2 = 7$ |
| 4α-H | 4.5 | m | 1 | | 5.80 | dd | $J_1 = 3, J_2 = 5$ |
| 3α-H | 3.2 | dt | 1 | $J_1 = 5, J_2 = 7.5$ | 3.55 | dt | $J_1 = 5, J_2 = 8$ |
| 3-CH$_2$CO$_2$H | 2.65 | d | 2 | $J = 6.5$ | 2.80 | | 1st proton:$J_1 = 5, J_2 = 17$ 2nd proton:$J_1 = 7.5, J_2 = 17$ |

EXAMPLES 4–9

By carrying out a similar hydrolysis to that described in Example 3, but using the corresponding 3,3aα,6,6aα-tetrahydrofuro[3,4-b]furan-2,4-dione derivatives of the formula:

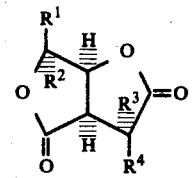

the following acids of formula I were obtained:

| Example | $R^1$ | $R^2$ | $R^3$ | $R^4$ | $R^5$ | $R^6$ | $R^7$ | $R^8$ | m.p. °C. | Note |
|---|---|---|---|---|---|---|---|---|---|---|
| 4 | H | n-Decyl | H | H | Direct Bond | | H | OH | 104–106 | A |
| 5 | Ph | H | H | Me | Direct Bond | | H | OH | 167–170 | B |
| 6 | Ph | H | H | Me | H | OH | Direct Bond | | 196–198 | C |
| 7 | n-Butyl | H | H | Me | Direct Bond | | H | OH | 164–167 | D |
| 8 | n-Butyl | H | =CH$_2$ | | Direct Bond | | H | OH | 118–121 | E |
| 9 | H | n-Pr | H | Me | Direct Bond | | H | OH | 108–110 | F |

Notes:
The following notes refer to the differences in procedure to that used in Example 3.
A: This hydrolysis was carried out on (±)-6α-n-decyl-3,3aα,6,6aα-tetrahydrofuro[3,4-b]furan-2,4-dione in a solution containing 40% v/v acetone in water for 2 hours at 25°C. and at pH 11. The hydrolysed material was purified by preparative layer chromatography (PLC) on silica (2mm. thick; hydrolysate loaded at rate of 150mg. per 20 × 20cm. plate) using a mixture (90:5:5 v/v) of chloroform, methanol and acetic acid. The band of $R_f$ 0.4–0.6 was extracted with cold ethyl acetate. The extracts were evaporated and purified by recrystallisation from a cold mixture of ethyl acetate and petrol to give (±)-2-(5α-n-decyl-4β-hydroxy-2-oxo-tetrahydrofuran-3β-yl)-acetic acid (Example 4).
B: This hydrolysis was carried out on (±)-6β-phenyl-3β-methyl-3,3aα,6,6aα-tetrahydrofuro[3,4-b]furan-2,4-dione in a solution containing 10% v/v acetonitrile in water at 25° C. for 40 minutes. The crude material obtained by extraction of the hydrolysis as in Example 3 was triturated with a mixture of acetone and ethyl acetate, and the solid thereby obtained was then crystallised from cold acetone to give (±)-2-(5β-phenyl-4β-hydroxy-2-oxo-tetrahydrofuran-3β-yl)-2β-methylacetic acid (Example 5), which had the following characteristic NMR spectrum:-

| | $d_6$-acetone | | | | $D_6$-acetone + TCAI | | |
|---|---|---|---|---|---|---|---|
| Signal | δ | Type | Proton No. | Coupling Constant ($H_z$) | δ | Type | Coupling Constant ($H_z$) |
| 5β-phenyl | 7.33 | m | 5 | | 7.33 | m | |
| 5α-H | 5.52 | d | 1 | $J=3$ | 5.87 | d | $J=3$ |
| (H) | 2.78 | dq | 1 | $J_1=10, J_2=7$ | 3.40 | dq | $J_1=10, J_2=7$ |
| 3β-C—CO$_2$H $\vert$ CH$_3$ H | 1.23 | d | 3 | $J=7$ | 1.37 | d | $J=7$ |
| 3β-C—CO$_2$H (CH$_3$) | | | | | | | |
| 4α-H | 4.65 | dd | 1 | $J_1=3, J_2=4.5$ | 5.52 | dd | $J_1=3, J_2=4.5$ |
| 3α-H | 3.22 | dd | 1 | $J_1=4.5, J_2=7$ | 3.92 | dd | $J_1=4.5, J_2=7$ |

C: The acetone and ethyl acetate filtrate, obtained from the trituration of the crude hydrolysis product in Example 5 (Note B), was concentrated and purified by PLC, using the system described in Note A. The band of $R_f$ 0.35 was extracted with cold ethyl acetate and purified, (after evaporation of the extracts) by trituration with ether, to give (±)-3β-methyl-5β-(β-phenyl)hydroxymethyl-2-oxo-tetrahydrofuran-4β-ylcarboxylic acid (Example 6) having the following characteristic NMR spectrum:-

| $d_6$-acetone | $d_6$-acetone + TCAI |
|---|---|

-continued

| Signal | δ | Type | Proton No. | Coupling Constant (H$_z$) | δ | Type | Coupling Constant (H$_z$) |
|---|---|---|---|---|---|---|---|
| 5β-{HO—C(Ph)(≡)H} | 7.40 | m | 5 | | 7.40 | m | |
| 5β-{HO—C(Ph)(≡)(H)} | 5.12 | d | 1 | J=9.0 | 6.30 | d | J=9.0 |
| 3α-H | 3.17 | dq | 1 | J$_1$=8, J$_2$=7 | 3.30 | dq | J$_1$=8, J$_2$=7 |
| 3β-CH$_3$ | 1.10 | d | 3 | J=7 | 1.15 | d | J=7 |
| 5α-H | 4.70 | dd | 1 | J$_1$=9, J$_2$=4.5 | 5.10 | dd | J$_1$=9, J$_2$=4.5 |
| 4α-H | 2.90 | dd | 1 | J$_1$=4.5, J$_2$=8 | 3.07 | dd | J$_1$=4.5, J$_2$=8 |

D: This hydrolysis was carried out at pH 9 on optically active 6β-n-butyl-3β-methyl-3,3aα,6,6aα-tetrahydrofuro[3,4-b]furan-2,4-dione in a solution containing 60% v/v methanol in water for 45 minutes at 20° C. The extracted hydrolysed material was purified by PLC on silica (0.5mm. thick; hydrolysate loaded at rate of 100mg. per 20 × 20cm. plate), using a mixture (95:4:1 v/v) of chloroform, acetone and 98% formic acid. The band of R$_f$ 0.1 was extracted with cold ethyl acetate. The extracts were evaporated and the residue purified by crystallisation as Example 3 to give 2-(5β-n-butyl-4β-hydroxy-2-oxo-tetrahydrofuran-3β-yl)-2β-methylacetic acid, (Example 7), [α]$_D^{28}$ + 52° (c, 1.1, methanol) having the following characteristic NMR spectrum:-

| Signal | d$_6$-acetone | | | | d$_6$-acetone + TCAI | | |
|---|---|---|---|---|---|---|---|
| | δ | Type | Proton No. | Coupling Constant (H$_z$) | δ | Type | Coupling Constant (H$_z$) |
| 5β-n-Butyl | 0.9–1.74 | m | 9 | | 0.9–1.74 | m | |
| 5α-H | 4.36 | dt | 1 | J$_1$=3, J$_2$=7 | 4.73 | dt | J$_1$=3, J$_2$=7 |
| 3β—C(H)(≡)—CO$_2$H, CH$_3$ | 2.76 | dq | 1 | J$_1$=6.5, J$_2$=10 | 2.76 | dq | J$_1$=6.5, J$_2$=10 |
| 3β-C(H)(≡)—CO$_2$H, (CH$_3$) | 1.28 | d | 3 | J=7 | 1.28 | d | J=7 |
| 4α-H | 4.50 | dd | 1 | J$_1$=3, J$_2$=4.5 | 5.85 | dd | J$_1$=3, J$_2$=4.5 |
| 3α-H | 3.04 | dd | 1 | J$_1$=4.5, J$_2$=10 | 3.55 | dd | J$_1$=4.5, J$_2$=10 |

E: This hydrolysis was carried out at pH 10 on optically active 6β-n-butyl-3-methylene-3,3aα,6,6aα-tetrahydrofuro-[3,4-b]furan-2,4-dione (canadensolide) in a solution containing 5% v/v acetonitrile in water at 2° C. for 1 hour. The extracted, hydrolysed material was purified by PLC on silica (0.5 mm. thick; hydrolysate loaded at rate of 200mg. per 20 × 40 cm. plate) in the same solvent mixture specified in Note D. The band of R$_f$ 0.5 was extracted with cold ethyl acetate, the extracts were evaporated and the residue was purified by crystallisation from a cold mixture of ether and petrol, to give 2-(5β-n-butyl-4β-hydroxy-2-oxo-tetrahydrofuran-3β-yl)-2-methylene-acetic acid (Example 8), having the following characteristic NMR spectrum:-

| Signal | d$_6$-acetone | | | | d$_6$-acetone + TCAI | | |
|---|---|---|---|---|---|---|---|
| | δ | Type | Proton No. | Coupling Constant (H$_z$) | δ | Type | Coupling Constant (H$_z$) |
| 5β-n-butyl | 0.90–1.90 | m | 9 | | 0.90–1.90 | m | |
| 5α-H | 4.45 | m | 1 | | 4.75 | | J$_1$=3.0, J$_2$=7.0 |
| 3β-C(=C)(CO$_2$H)(H)(H) | 5.99 | d | 1 | J=0.5 | 5.95 | d | J=0.5 |
| 3β-C(=C)(CO$_2$H)(H)(H) | 6.53 | d | 1 | J=0.5 | 6.50 | d | J=0.5 |
| 4α-H | 4.45 | m | 1 | | 5.67 | dd | J$_1$=4.5, J$_2$=3.0 |
| 3α-H | 3.97 | dt | 1 | J$_1$=4.5 | 4.30 | dt | J$_1$=4.5 |

|  | $d_6$-acetone | | | | $d_6$-acetone + TCAI | | |
|---|---|---|---|---|---|---|---|
| Signal | δ | Type | Proton No. | Coupling Constant ($H_z$) | δ | Type | Coupling Constant ($H_z$) |
| | | | | $J_2 = 0.5$ | | | $J_2 = 0.5$ |

F: This hydrolysis was carried out at pH 10 on (±)-6α-n-propyl-3β-methyl-3,3aα,6,6aα-tetrahydrofuro[3,4-b]furan-2,4-dione in a solution containing 4% v/v of acetonitrile in water for 15 minutes at 25° C. The extracted, hydrolysed material was purified by recrystallisation from a cold mixture of ethly acetate and petrol to give (±)-2-(5α-n-propyl-4αhydroxy-2-oxo-tetrahydrofuran-3β-yl)-2βmethylacetic acid (Example 9), having the following characteristic NMR spectrum:-

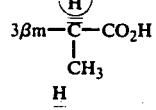

| Signal | $d_6$-acetone | | | | $d_6$-acetone + TCAI | | |
|---|---|---|---|---|---|---|---|
| | δ | Type | Proton No. | Coupling Constant ($H_z$) | δ | Type | Coupling Constant ($H_z$) |
| 5α-n-propyl | 0.90-1.75 | m | 7 | | 0.90-1.75 | m | |
| 5β-H | 4.33 | m | 1 | | 4.75 | t | J=7 |
| 3βm—C(H)—CO₂H, CH₃ | 2.80 | dq | 1 | $J_1=7$, $J_2=10$ | 2.95 | dq | $J_1=7$, $J_2=10$ |
| 3β—C(H)—CO₂H, CH₃ | 1.30 | d | 3 | J=7 | 1.40 | d | J=7 |
| 4α-H | 4.4 | m | 1 | | 5.55 | d | J=5 |
| 3α-H | 3.02 | dd | 1 | $J_1=10$, $J_2=5$ | 3.65 | dd | $J_1=10$, $J_2=5$ |

EXAMPLE 10

A solution of (+)-3β-carboxy-4β,5β-dihydroxy-2α-methyl-nonanoic acid (100mg.) in acetone (10ml.) was heated under reflux for 4 hours and the solvent evaporated at 50° C. The residue was dissolved in an aqueous buffer solution (10ml.) at pH 6, the buffer solution containing 0.1M citric acid and 0.2M disodium hydrogen phosphate. After extraction with ether, the aqueous phase was adjusted to pH 4 with 0.1M aqueous citric acid solution and extracted with ethyl acetate (2 × 10ml.). The ethyl acetate extracts were dried (Na₂SO₄) and evaporated. The solid residue was then purified by High Pressure Liquid Chromatography using a "μ-Bondapak" (Trade-mark) C18, column (supplied by Waters Associates Inc., Maple Street, Milford, Massachussets, U.S.A.), a mixture (2:18:80 v/v) of acetic acid, acetonitrile and water as eluant, and a flow rate of 1ml./minute. Fractions (1ml.) were then collected. Fractions 14 and 15 were combined and evaporated. The solid residue obtained was recrystallised from a mixture of cold acetone and petrol to give (+)-2-(5β-n-butyl-4β-hydroxy-2-oxo-tetrahydrofuran-3β-yl)-2α-methylacetic acid, m.p. 114°–116° C., $[\alpha]_D^{28}$ +77 (c, 2.5; methanol) having the following characteristic NMR spectrum:

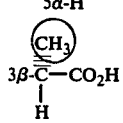

| Signal | $d_6$-acetone | | | | $d_6$-acetone + TCAI | | |
|---|---|---|---|---|---|---|---|
| | δ | Type | Proton No. ($H_z$) | Coupling Constant δ | Type | ($H_z$) | Coupling Constant |
| 5β-n-butyl | 0.89-1.72 | m | 9 | | 0.90-1.72 | m | |
| 5α-H | 4.31 | dt | 1 | $J_1=3$, $J_2=7$ | 4.6 | dt | $J_1=3$, $J_2=7$ |
| 3β-C(CH₃)—CO₂H, H | 1.46 | d | 3 | J=6.5 | 1.46 | d | J=6.5 |
| 3β—C(CH₃)—CO₂H, H | 2.86 | m | 1 | | 2.86 | dq | $J_1=6.5$, $J_2=10$ |
| 4α-H | 4.49 | dd | 1 | $J_1=3$, $J_2=4.5$ | 5.75 | dd | $J_1=3$, $J_2=4.5$ |
| 3α-H | 2.86 | m | 1 | | 3.2 | dd | $J_1=4.5$, $J_2=10$ |

EXAMPLE 11

Combination of fractions 11–13 from the HPLC in Example 10 followed by evaporation gave a solid from which 3α-methyl-5β-(1β-hydroxy-n-pentyl)-2-oxo-tetrahydrofuran-4β-ylcarboxylic acid was isolated by crystallisation from a cold mixture of acetone and petrol. This material was identical with that obtained in Example 1 and had $[\alpha]_D^{24}$ −113° (c, 2.7, MeOH), and the following characteristic NMR spectrum:

| Signal | d$_6$-acetone | | | | d$_6$-acetone + TCAI | | |
|---|---|---|---|---|---|---|---|
| | δ | Type | Proton No. | Coupling Constant (H$_z$) | δ | Type | Coupling Constant (H$_z$) |
| 5β-{HO—C(n-Bu)—H} | 0.90-1.80 | m | 9 | | 0.90-1.80 | m | |
| 5β-{HO—C(n-Bu)—(H)} | 3.98 | dt | 1-1 | J$_1$=7, J$_2$=2 | 5.22 | dt | J$_1$=7, J$_2$=2 |
| 3β-H | 3.20 | m | 1 | | 3.20 | dq | J$_1$=7, J$_2$=10 |
| 3α-CH$_3$ | 1.20 | d | 3 | J=7 | 1.20 | d | J=7 |
| 5α-H | 4.60 | dd | 1 | J$_1$=2, J$_2$=8.5 | 4.87 | dd | J$_1$=2, J$_2$=8.5 |
| 4α-H | 3.22 | m | 1 | | 3.48 | dd | J$_1$=8.5, J$_2$=10 |

EXAMPLE 12

Using a similar procedure to that described in Example 3, hydrolysis of optically active dihydrocanadensolide (6β-n-butyl-3α-methyl-3,3aα,6,6aα-tetrahydrofuro[3,4-b]furan-2,4-dione) at pH 9-10 in a mixture (4:1 v/v) of methanol and water at 20° C. for 1 hour, gave after purification by HPLC (as described in Example 10):

(a) (−)-3α-methyl-5β-(1β-hydroxy-n-pentyl)-2-oxo-tetrahydrofuran-4β-ylcarboxylic acid, identical with that obtained in Example 11; and (b) (+)-2-(5β-n-butyl-4β-hydroxy-2-oxo-tetrahydrofuran-3β-yl)-2α-methylacetic acid, identical with that obtained in Example 10.

EXAMPLE 13

A stirred solution of (+)-2-(5β-n-butyl-4β-hydroxy-2-oxo-tetrahydrofuran-3β-yl)-2α-methylacetic acid (10 mM) in a minimum volume of acetone at 25° C. was treated dropwise with 10mM of a 0.1M aqueous solution of sodium hydroxide. The acetone was evaporated and the aqueous residue was first extracted with ethyl acetate, and then itself evaporated to dryness. There was thus obtained sodium (+)-2-(5β-n-butyl-4β-hydroxy-2-oxo-tetrahydrofuran-3β-yl)-2α-methylacetate, as a white powder, m.p. 279° C.

In a similar manner, there was obtained the sodium salt of (+)-3α-methyl-5β-(1β-hydroxy-n-pentyl)-2-oxo-tetrahydrofuran-4β-ylcarboxylic acid, m.p. 269° C.

EXAMPLE 14

A solution of (+)-2-(5β-n-butyl-4β-hydroxy-2-oxo-tetrahydrofuran-3β-yl)-2α-methylacetic acid (0.5g.) in a minimum volume of acetone was mixed at 20°-25° C. with an excess of diethylamine (1ml.). The solution was immediately evaporated to give crystalline diethylamine (+)-2-(5α-n-butyl-4β-hydroxy-2-oxo-tetrahydrofuran-3β-yl)-2α-methylacetate, m.p. 97°-100° C. (after recrystallisation from ether).

In a similar manner, the diethylamine salt of (−)-3α-methyl-5β-(1β-hydroxy-m-pentyl)-2-oxo-tetrahydrofuran-4β-ylcarboxylic acid was obtained as a crystalline solid, m.p. 110°-116° C. (after recrystallisation from ethyl acetate).

EXAMPLE 1

A solution of benzyl 2-(5β-n-butyl-4β-hydroxy-2-oxo-tetrahydrofuran-3β-yl)-2α-methyl-acetate (50mg.) in methanol (25ml.) was mixed with palladium-charcoal (30% w/w). The mixture was then hydrogenated at 20°-25° C. until one molecular equivalent of hydrogen was consumed. The mixture was filtered and the filtrate evaporated to give, after crystallisation from cold acetone and petrol, 2-(5β-n-butyl-4β-hydroxy-2-oxo-tetrahydrofuran-3β-yl)-2α-methyl-acetic acid, m.p. 114°-116° C.

The starting benzyl ester was obtained as follows:

A solution of sodium 2-(5β-n-butyl-4β-hydroxy-2-oxo-tetrahydrofuran-3β-yl)-2α-methyl-acetate (1mM) in dimethylformamide (10ml.; dried over sodium aluminium silicate) was mixed with benzyl bromide (1mM) at 20°-25° C. After 15 minutes the mixture was evaporated to dryness and the residue was partitioned between water (25ml.) and ether (25ml.). Evaporation of the ether and recrystallisation of the residue from a mixture of ether and petrol gave benzyl 2-(5β-n-butyl-4β-hydroxy-2-oxo-tetrahydrofuran-3β-yl)-2α-methyl acetate, m.p. 65° C.

EXAMPLE 16

A similar hydrolysis to that described in Example 3 was performed on (+)-2-(5β-n-butyl-4β-hydroxy-2-oxo-tetrahydrofuran-3β-yl)-2α-methyl-acetic acid at pH 9-10 in a solution containing 5% v/v acetonitrile in water at 20°-25° C. for 3 hours. The pH of the solution was then adjusted to 3.5 with concentrated hydrochloric acid. The mixture was then extracted with ethyl acetate and the combined extracts were dried (Na$_2$SO$_4$), and evaporated to give (+)-3β-carboxy-4β,5β-dihydroxy-2α-methylnonanoic acid, m.p. 132°-133° C. (crystallised from a cold mixture of acetone and petrol).

EXAMPLE 17

A mixture of (+)-2-(5β-n-butyl-4β-hydroxy-2-oxo-tetrahydrofuran-3β-yl)-2α-methylacetic acid (200 parts by weight) and micro-crystalline cellulose (800 parts by weight) was sieved through a 30 mesh screen. Magnesium stearate (60 mesh particle size) (10 parts by weight) was then added and, after thorough mixing, the resultant mass was compressed into tablets. There were thus obtained tablets, each weighing 1.0g. and containing 200mg. of active ingredient, which may be administered orally to man for therapeutic purposes.

EXAMPLE 18

In a similar manner to that described in Example 17, there were obtained tablets, weighing 1.0g. and containing (−)-3α-methyl-5β-(1β-hydroxy-n-pentyl)-2-oxo-tetrahydrofuran-4β-ylcarboxylic acid, which were suitable for oral administration to man for therapeutic purposes.

EXAMPLE 19

The tablets obtained by the process of Example 17 or Example 18 were film coated by conventional means by spraying with a mixture prepared by adding a dispersion of titanium dioxide in glycerol to a solution of hydroxypropylmethylcellulose in a mixture of methanol (30 parts v/v) and methylene chloride (70 parts v/v) to give a final concentration of:
  hydroxypropylmethylcellulose; 2% w/v
  glycerol; 0.4% w/v
  titanium dioxide; 0.6% w/v
There were thus obtained film coated tablets, containing 200mg. of active ingredient, which are suitable for oral administration to man for therapeutic purposes.

EXAMPLE 20

The procedure described in Example 19 was repeated using tablets obtained in Example 17 or 18, except that the hydroxypropylmethylcellulose was replaced by hydroxypropylmethylcellulose phthalate (5% w/v) in the spray solution, there were thus obtained tablets, which are enteric film coated, and which contain 200mg. of active ingredient and are suitable for oral administration to man for therapeutic purposes.

What we claim is:

1. A mono-lactone of the formula:

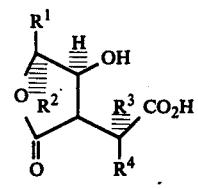

[II]

wherein one of $R^1$ and $R^2$ is hydrogen, a $C_{1-10}$-alkyl or phenyl radical, and the other of $R^1$ and $R^2$ is hydrogen; one of $R^3$ and $R^4$ is hydrogen or a $C_{1-6}$-alkyl radical, and the other $R^3$ and $R^4$ is hydrogen; or $R^3$ and $R^4$ together form the methylene ($=CH_2$) radical or a pharmaceutically acceptable base addition salt thereof.

2. A compound according to claim 1 wherein $R^1$ is an n-butyl or phenyl radical, $R^2$ is hydrogen, one of $R^3$ and $R^4$ is a methyl radical, and the other of $R^3$ and $R^4$ is hydrogen; or a pharmaceutically-acceptable base addition salt thereof.

3. The compound 2-(5β-n-butyl-4β-hydroxy-2-oxo-tetrahydrofuran-3β-yl)-2α-methyl-acetic acid or a pharmaceutically-acceptable base addition salt thereof.

4. The compound 2-(5β-phenyl-4β-hydroxy-2-oxo-tetrahydrofuran-3β-yl)-2β-methyl-acetic acid or a pharmaceutically-acceptable base addition salt thereof.

5. A pharmaceutical composition for use in the treatment of duodenal or gastric ulcers which comprises as active ingredient an effective amount of a compound as claimed in claim 1, or a pharmaceutically-acceptable base addition salt thereof, together with a pharmaceutically-acceptable diluent or carrier.

6. A method for the treatment of duodenal or gastric ulcers in warm-blooded animals which comprises administering to the said animals an effective amount of a composition as claimed in claim 5.

* * * * *